United States Patent [19]

Rubin

[11] Patent Number: 4,526,902
[45] Date of Patent: Jul. 2, 1985

[54] COMBINED FATTY ACID COMPOSITION FOR TREATMENT OR PROPHYLAXIS OF THROMBO-EMBOLIC CONDITIONS

[75] Inventor: David Rubin, Jerusalem, Israel

[73] Assignee: Century Laboratories, Inc., Port Washington, N.Y.

[21] Appl. No.: 545,349

[22] Filed: Oct. 24, 1983

[51] Int. Cl.³ ............................................. A61K 31/23
[52] U.S. Cl. .................................................... 514/560
[58] Field of Search ................................ 424/312, 318

[56] References Cited

U.S. PATENT DOCUMENTS 4,097,602  6/1978  Silver et al. ......................... 424/305

FOREIGN PATENT DOCUMENTS 1082624  6/1967  United Kingdom .
2033745  5/1980  United Kingdom ................ 424/312
1604554  12/1981  United Kingdom ................ 424/312

OTHER PUBLICATIONS

Chemical Abstracts, 96:5376u, (1982).
Chemical Abstracts, 94:41534m, (1981).
Chemical Abstracts, 92:55857q, (1980).
Chemical Abstracts, 90:48800w, (1979).
Dyerberg, J. et al., α-Linolenic Acid and Eicosapentaenoic Acid, Lancet, pp. 199–200, (Jan. 1980).

Primary Examiner—Frederick E. Waddell
Attorney, Agent, or Firm—Browdy and Neimark

[57] ABSTRACT

Treatment of prophylaxis of thrombo-embolic conditions is obtained through the simultaneous administration of eicosapentaenoic acid and/or docosahexaenoic acid together with one or more of linoleic acid, γ-linolenic acid and dihomo-γ-linolenic acid, either in the form of a pharmaceutical dosage or in the form of a food product such as margarine or cooking oil.

9 Claims, No Drawings

COMBINED FATTY ACID COMPOSITION FOR TREATMENT OR PROPHYLAXIS OF THROMBO-EMBOLIC CONDITIONS

FIELD OF THE INVENTION

The present invention relates to pharmaceutical compositions or food products, and, more particularly, to such compositions or food products containing a specific combination of fatty acids which can be used to treat or provide effective prophylaxis against thrombo-embolic conditions.

BACKGROUND OF THE INVENTION

It is known that Greenland Eskimos rarely suffer from atherosclerotic cardiovascular diseases. This fact has been attributed to the consumption of high amounts of fish oil. The active ingredients in fish oil are (all-Z)-5,8,11,14,17-eicosapentaenoic acid (hereinafter EPA) and 22:6ω3-docosahexaenoic acid (hereinafter DHA). EPA and DHA are known to be precursors in the biosynthesis of the prostaglandin $PGE_3$.

It is disclosed in British Pat. Nos. 1,604,554 and 2,033,745 that EPA can be used to treat effectively, or provide effective prophylaxis against, thrombo-embolic conditions such as myocardial infarctions, strokes, or deep vein thrombosis during surgical operations. They disclose the extraction of EPA from fish oil, such as cod liver oil or menhaden oil. The EPA may be administered by replacing butter or ordinary margarine by a special margarine formulated so that in normal usage the recipient would receive the required amount of the EPA.

This process has not achieved widespread attention, despite the fact that it uses a natural substance which can readily be incorporated into the daily diet. One reason may be due to the difficulty of efficiently separating EPA from natural fish oils to obtain a pure product at reasonable cost. Another reason may be that the effects of administration of EPA are not as dramatic as anticipated.

SUMMARY OF THE INVENTION

It is an object of the present invention to eliminate the above-discussed deficiencies in the prior art.

It is another object of the present invention to provide improvements in compositions of the type of British Pat. Nos. 1,604,554 and 2,033,745.

It is a further object of the present invention to provide a composition which has superior therapeutic effects compared to those of the prior art.

It is yet another object of the present invention to provide a therapeutic composition containing naturally obtainable fatty acids which will serve to reduce thromboembolic phenomena and athero-sclerotic processes.

It is still another object of the present invention to provide a therapeutic composition which will increase the $PGE_1$: $PGE_2$ ratio in the patient, and increase the absolute amount of $PGE_1$ in the system.

These and other objects are obtained through the simultaneous administration of EPA and/or DHA together with one or more of linoleic acid ((Z,Z)-9,12-octadecadienoic acid), γ-linolenic acid ((Z,Z,Z)-6,9,12-octadecatrienoic acid), and dihomo-γ-linolenic acid (8,11-14-eicosatrienoic acid), the latter being hereinafter referred to as DHLA, either in the form of a pharmaceutical dosage or in the form of a food product such as margarine or cooking oil, or in the form of a skin ointment or lotion for topical administration.

DETAILED DESCRIPTION OF PREFERRED EMBODIMENTS

The prostaglandins are a family of substances showing a wide diversity of biological effects. Prostaglandins of the 1-, 2- and 3-series, respectively, incorporate one, two or three double bonds in their basic 20-carbon carboxylic fatty acid structure which incorporates a 5-member cyclopentene ring.

The 1-series of prostaglandins are strong vasodilators and inhibit cholesterol and collagen biosynthesis, as well as platelet aggregation. On the other hand the 2-series prostaglandins are known to enhance platelet aggregation, cholesterol and collagen biosynthesis, and also to enhance endothelial cell proliferation. The main effect of the 3-series prostaglandins, particularly $PGE_3$, is the suppression of the 2-series prostaglandins.

The precursor of the 2-series prostaglandins is arachidonic acid ((all Z)-5,8,11,14-eicosatetraenoic acid). DHLA is the precursor for the 1-series prostaglandins, and, as indicated hereinabove, EPA and DHA are precursors for the 3-series prostaglandins.

It is believed that the effectiveness of EPA and DHA in preventing athero-sclerotic cardio-vascular diseases lies both in their effect as precursors for prostaglandin $PGE_3$, which suppresses the 2-series prostaglandins, as well as the fact that the EPA and/or DHA itself competes with arachidonic acid on the same enzymatic system and thus inhibits the biosynthesis of 2-series prostalandins. This inhibition of the 2-series prostaglandins results in an increase of the ratio of $PGE_1$: $PGE_2$.

In order to improve the effects of the administration of EPA and/or DHA alone, by further increasing the $PGE_1$: $PGE_2$ ratio, as well as effecting an increase in the absolute amount of $PGE_1$ in the system, DHLA should be administered simultaneously with the pure EPA and/or DHA. Since linoleic acid and γ-linolenic acid both form DHLA metabolically within the body, either or both of these fatty acids may be substituted, in whole or in part, for DHLA.

Not only will the combination of EPA (and/or DHA) and DHLA (and/or linoleic acid and/or γ-linolenic acid) cause a reduction in thrombo-embolic phenomena and athero-sclerotic processes, but it is expected that such a composition will have other beneficial therapeutic properties. For example, it is known that in schizophrenia, rheumatoid arthritis and other collagen and autoimmune diseases, as well as in some forms of cancer, there are evidences of extremely low levels of $PGE_1$ and high levels of $PGE_2$. Thus, it is expected that the combination of the present invention may be able to serve as an effective treatment for such conditions. Furthermore, the anti-infammatory effect of corticosteroids and the pain killing effect of aspirin are believed to be due to their suppressing effect of $PGE_2$ formation. Thus, the use of the combination of the present invention can be expected to be a natural and most effective anti-inflammatory pain killing agent.

The dose of the composition of the present invention, comprising a combination of EPA (and/or DHA) and DHLA (and/or linoleic acid and/or γ-linolenic acid), needed for therapeutic or prophylactic effect will vary with the route of administration and the nature of the condition being treated, but will generally be at least 1 gram, preferably from 1.5 to 3 grams, per day. This is the dose for an average 70 kg man, and the dose for other men or animals will vary pro rata according to their weight, i.e. about 20–40 mg/kg.

The relative amounts of EPA (and/or DHA) and DHLA (and/or linoleic acid and/or γ-linolenic acid) in the composition of the present invention is preferably 1:1, although the ratio may vary from 3:1 to 1:3.

The EPA (and/or DHA) and DHLA (and/or linoleic acid and/or γ-linolenic acid) need not be administered as the acids themselves but may be used as their pharmaceutically acceptable salts, esters or amides. Esters or amides which can be converted in vivo to the acid and other pharamaceutically acceptable products may be used, the preferred ester being the ethyl ester. The preferred salts are the sodium or potassium salts, or any other pharmaceutically acceptable solid salt, as these are suitable for making into tablets.

While it is preferred to administer the composition of the present invention orally, as this is a convenient route for routine administration, the active compounds may be administered by any route by which it may be successfully absorbed, e.g., parenterally (i.e. subcutaneously, intramuscularly or intravenously), rectally or vaginally or topically, for example, as a skin ointment or lotion.

While it is possible for the active compounds to be administered as such, as a simple mixture of components, it is preferable to present them as a pharmaceutical formulation. The formulations, both for veterinary and for human medical use, of the present invention comprise the active compounds as defined, together with one or more pharmaceutically acceptable carriers therefor and, optionally, other therapeutic ingredients, although other unsaturated fatty acids should be avoided. The carrier(s) must be "pharmaceutically acceptable" in the sense of being compatible with the other ingredients of the formulations and not deleterious to the recipient thereof. Formulations include those suitable for oral, rectal, vaginal, intrapulmonary or parenteral (including subcutaneous, intramuscular and intravenous) administration. Formulations for oral administration, such as tablets or capsules, are preferred.

The EPA (and/or DHA)-DHLA (and or linoleic acid and/or γ-linolenic acid) combination may also be administered by replacing butter and/or ordinary margarine by a special margarine, e.g. of the emulsion type, formulated so that in normal usage the recipient would receive the required amount of the combination. Cooking oils and fats may also be similarly formulated to contain the composition of the present invention.

The EPA (and/or DHA) and DHLA (and/or linoleic acid and/or γ-linolenic acid) used in the compositions of the present invention should be as pure as possible. EPA (and/or DHA) cannot be used in the form of fish oil directly, as the use of the amount of fish oil necessary in order to provide the desired amount of EPA (and/or DHA) would provide excessive calories and potentially toxic amounts of vitamins A and D. Thus, pure EPA (and/or DHA) should be extracted from the fish oil. The presence of unsaturated fatty acids other than EPA, DHA, DHLA, linoleic acid and γ-linolenic acid should be avoided.

A novel way of extracting EPA and DHA from fish oil, such as cod liver oil, or for separating any combination of unsaturated fatty acids is described in detail in the copending application of the present inventor filed on even date herewith, Ser. No. 545,350, entitled "Method for Separation of Fatty Acids from Natural Fats and Fatty Acids", the entire contents of which are hereby incorporated by reference.

In order to protect the fatty acids from oxidation throughout the extraction procedure, and to increase the resolution and thus facilitate the separation of the otherwise difficult to isolate fatty acids, the double bonds of the unsaturated fatty acids are initially iodinated. This principle holds true for the separation and extraction of α-linolenic and γ-linolenic acids from the triglyeride or other forms in which they occur. For example, γ-linolenic acid can be extracted in pure form from oil of evening primrose, or any other oil in which it naturally occurs. The separation takes place on column chromatography as follows.

A 20% ethanolic solution of iodine is added slowly to 300 g of cod liver oil. The iodine is added as long as its color disappears in the oil. The reaction takes place at room temperature under continuous stirring. When iodination is completed, the iodinated oily solution is saponified with 20% ethanolic solution of KOH for 2 hours. The iodinated fatty acid, 260 g, is extracted with ease from the saponification mixture.

The iodinated fatty acids are then methylated with 5% hydrogen chloride in methanol. The EPA and the docosahexaenoic acid (DHA) are separated by column chromatography (silica-gel 1,500 g, Kieselgel 70-230 mesh, Merck). The elution is done with 5 liters hexane-ether-acetic acid (85-10-5). The first fraction to be extracted is the iodinated DHA. The second fraction is iodinated EPA.

Deiodination takes place by shaking the iodinated Me-DHA and Me-EPA separately with 10% aqueous solution of silver nitrate. A precipitate of silver-iodine appears and the organic phase is separated. The same procedure is repeated until no more precipitation occurs. Microanalysis, HPLC and NMR prove that the desired products are obtained. The yield is above 90%, the purity 96–100%. There is no need to carry out the procedure under nitrogen since the fatty acids are saturated with iodine, thus preventing oxidation from taking place.

Once the substantially pure methylated and iodinated fatty acid mixture is obtained, it may also be separated by other conventional techniques, such as high speed centrifugation or distillation.

It will be obvious to those skilled in the art that various changes may be made without departing from the scope of the invention and the invention is not to be considered limited to what is described in the specification.

What is claimed is:

1. A pharmaceutical composition for treatment or prophylaxis of thrombo-embolic conditions consisting essentially of an effective amount of a combination of a first component selected from the group consisting of 5, 8, 11, 14, 17-eicosapentaenoic acid, 22:6 ω 3-docosahexaenoic acid and a combination thereof, and a second component selected from the group consisting of linoleic acid, γ-linolenic acid, dihomo-γ-linolenic acid and combinations thereof, said first and second components being present in relative amounts of 3:1 to 1:3.

2. A composition in accordance with claim 1, further includng a pharmaceutically acceptable excipient.

3. A composition in accordance with claim 1, wherein said composition is substantially free of other unsaturated fatty acids.

4. In a food product containing a substantial amount of at least one fatty acid, the improvement wherein said at least one fatty acid present in said food product consists essentially of a combination of a first component selected from the group consisting of 5,8,11,14,17-eicosapentaenoic acid, 22:6 ω 3 docosahexaenoic acid and a combination thereof, and a second component selected from the group consisting of linoleic acid, γ-linolenic acid, dihomo-γ-linolenic acid and combinations thereof, said first and second components being present in relative amounts of 3:1 to 1:3.

5. A food product in accordance with claim 4, wherein said food product is margarine.

6. A composition in accordance with claim 1, wherein said first component is 5,8,11,14,17-eicosapentaenoic acid.

7. A composition in accordance with claim 6, wherein said second component is linoleic acid.

8. A food product in accordance with claim 4, wherein said first component is 5,8,11,14,17-eicosapentaenoic acid.

9. A food product in accordance with claim 8, wherein said second component is linoleic acid.

* * * * *